United States Patent
Seng, Sr. et al.

(10) Patent No.: US 9,427,603 B2
(45) Date of Patent: *Aug. 30, 2016

(54) PROCESS FOR REDUCING HAIR DAMAGE UPON TREATMENT OF HAIR BY HEAT

(71) Applicant: The Procter & Gamble Company, Cincinnati, OH (US)

(72) Inventors: Juergen Seng, Sr., Kelkheim (DE); Christoph Schmitz, Laggoens (DE); Andreas Flohr, Kronberg (DE)

(73) Assignee: The Procter & Gamble Company, Cincinnati, OH (US)

( * ) Notice: Subject to any disclaimer, the term of this patent is extended or adjusted under 35 U.S.C. 154(b) by 56 days.

This patent is subject to a terminal disclaimer.

(21) Appl. No.: 14/569,133

(22) Filed: Dec. 12, 2014

(65) Prior Publication Data

US 2015/0083155 A1 Mar. 26, 2015
US 2016/0151271 A9 Jun. 2, 2016

Related U.S. Application Data

(63) Continuation of application No. 12/865,760, filed as application No. PCT/US2009/033747 on Feb. 11, 2009, now Pat. No. 8,940,282.

(30) Foreign Application Priority Data

Feb. 11, 2008 (EP) ..................... 08151246

(51) Int. Cl.
*A61Q 5/12* (2006.01)
*A61K 8/898* (2006.01)

(52) U.S. Cl.
CPC ................. *A61Q 5/12* (2013.01); *A61K 8/898* (2013.01); *A61K 2800/80* (2013.01)

(58) Field of Classification Search
None
See application file for complete search history.

(56) References Cited

U.S. PATENT DOCUMENTS

| | | | |
|---|---|---|---|
| 3,814,110 A | 6/1974 | Cassidy | |
| 3,976,588 A | 8/1976 | McLaughlin | |
| 4,066,746 A | 1/1978 | Callingham | |
| 4,135,524 A | 1/1979 | Rosenberg | |
| 4,183,367 A | 1/1980 | Goebel | |
| 4,563,347 A | 1/1986 | Starch | |
| 4,673,568 A | 6/1987 | Grollier | |
| 4,973,476 A | 11/1990 | Krzysik | |
| 5,567,428 A | 10/1996 | Hughes | |
| 5,968,286 A | 10/1999 | Crudele | |
| 6,056,946 A | 5/2000 | Crudele | |
| 6,136,304 A | 10/2000 | Pyles | |
| 6,207,141 B1 | 3/2001 | Pyles | |
| 6,451,747 B1 | 9/2002 | Decoster | |
| 6,824,765 B2 | 11/2004 | Gawtrey | |
| 7,223,385 B2 | 5/2007 | Gawtrey | |
| 8,197,799 B2 | 6/2012 | Tsotsoros | |
| 8,940,282 B2 * | 1/2015 | Seng et al. ................. | 424/70.12 |
| 2001/0023235 A1 | 9/2001 | Crudele | |
| 2001/0049849 A1 | 12/2001 | Mettrie | |
| 2003/0053975 A1 | 3/2003 | Eissmann | |
| 2004/0029984 A1 | 2/2004 | Johnson | |
| 2005/0232882 A1 | 10/2005 | Bebot | |
| 2006/0041026 A1 | 2/2006 | Mahr | |
| 2006/0088490 A1 | 4/2006 | Maruyama | |
| 2007/0141007 A1 | 6/2007 | Glynn | |
| 2007/0190009 A1 | 8/2007 | Guentert | |
| 2009/0226381 A1 | 9/2009 | Maillefer | |
| 2009/0269296 A1 | 10/2009 | Ivanova | |
| 2009/0285765 A1 | 11/2009 | Ivanova | |

FOREIGN PATENT DOCUMENTS

| | | |
|---|---|---|
| CA | 1123338 A1 | 5/1982 |
| EP | 477057 A1 | 3/1992 |
| JP | 01139522 A | 6/1989 |
| JP | 2000344633 A | 12/2000 |
| JP | 2001213741 A | 8/2001 |
| JP | 2003286137 A | 10/2003 |
| JP | 2006028112 A | 2/2006 |
| JP | 2006117579 A | 5/2006 |
| JP | 2006169164 A | 6/2006 |
| JP | 2006282518 A | 10/2006 |
| JP | 2007153806 A | 6/2007 |
| WO | WO9427570 A1 | 12/1994 |
| WO | WO0044337 A1 | 8/2000 |
| WO | WO2006000257 A1 | 1/2006 |
| WO | WO2006012930 A1 | 2/2006 |
| WO | WO2007029590 A1 | 3/2007 |

* cited by examiner

Primary Examiner — Jyothsna Venkat
(74) Attorney, Agent, or Firm — James T. Fondriest

(57) ABSTRACT

A process for reducing hair damage upon treatment of hair by heat comprising the steps of providing a hair care composition comprising a heat-stable silicone material, applying said composition onto hair, providing a heat generating hair care appliance, and treating hair using said appliance; use and kit thereof.

4 Claims, No Drawings

PROCESS FOR REDUCING HAIR DAMAGE UPON TREATMENT OF HAIR BY HEAT

FIELD OF THE INVENTION

According to a first aspect, the present invention relates to a process for reducing hair damage upon treatment of hair by heat comprising the steps of providing a hair care composition comprising a heat-stable silicone material, applying said composition onto hair, providing a heat generating hair care appliance, and treating hair using said appliance. According to second and third aspects, the invention relates to the uses of said composition and said heat-stable silicone material. According a fourth aspect, the invention relates to a kit comprising said hair care composition and said appliance. Said processes are useful for treating hair, such as drying and/or styling hair, by heat while protecting hair and/or reducing hair damage that may occur upon treatment of hair by heat.

BACKGROUND OF THE INVENTION

Heat generating hair care appliances, such as hot air hair care appliances and hot surface hair care appliances, are commonly used for drying and/or styling hair. Particularly, hot air hair care appliances are primarily used in order to dry hair. Particularly, hot surface hair care appliances are primarily used in order to style hair. Such appliances allow treating hair upon heat. The temperature may be superior to 50° C., or even 100° C.

However, hair are sensitive to temperature and treating hair using heat generating hair care appliances may alter the structure of hair fibers and, therefore, may damage hair. Particularly, repeated treatments using a heat generating hair care appliance at regular intervals increase the risk of damaging hair.

In order to prevent and/or reduce hair damage, the user may apply hair care compositions. It is known a wide range of various hair care compositions, e.g. shampoo, hair-conditioning compositions, hairstyling compositions. However, even if these compositions may reduce in some extent hair damage, these compositions are usually not suitable for reducing hair damage induced upon treatment by heat. In some cases, such compositions may even contribute to damaging hair, when applying in conjunction with a treatment of hair using a heat generating appliance, because they comprise components degrading under high temperature.

There is a continuous need, therefore, for providing process for reducing hair damage upon treatment of hair by heat.

SUMMARY OF THE INVENTION

According to a first aspect, the present invention relates to a process for reducing hair damage upon treatment of hair by heat comprising the steps of:
  providing a hair care composition comprising a heat-stable silicone material and a cosmetically acceptable carrier;
  applying onto hair a sufficient amount of hair care composition for treating hair;
  providing a heat generating hair care appliance;
  treating hair using the heat generating hair care appliance for a sufficient amount of time.

According to a second aspect, the present invention relates to the use of a hair care composition, according to the first aspect, for protecting hair and reducing hair damage upon treatment of hair by heat.

According to a third aspect, the present invention relates to the use of a heat-stable silicone material, according to the first aspect of the invention, for preparing a heat-styling hair care composition.

According to a fourth aspect, the present invention relates to a kit for reducing hair damage upon treatment of hair by heat comprising;
  a hair care composition, according to the first aspect, comprising a heat-stable silicone material and a cosmetically acceptable carrier;
  a heat-generating hair care appliance, preferably a hot air hair care appliance and/or a hot surface hair care appliance.

DETAILED DESCRIPTION OF THE INVENTION

According to a first aspect, the present invention relates to a process for reducing hair damage upon treatment of hair by heat comprising the steps of:
  providing a hair care composition comprising a heat-stable silicone material and a cosmetically acceptable carrier;
  applying onto hair a sufficient amount of hair care composition for treating hair;
  providing a heat generating hair care appliance;
  treating hair using the heat generating hair care appliance for a sufficient amount of time.

The inventors have surprisingly found that applying a hair care composition comprising a heat-stable silicone material before treating hair using a heat generating hair care appliance allows protecting hair against any damage that may occur upon treatment by heat. Indeed, heat generating hair care appliances, and particularly hot surface hair care appliances, may generate temperature above 50° C. or even 100° C. Such high temperature may alter the structure of hair fibers and, therefore, damage hair. Without wishing to be bound by theory, it is believed that heat-stable silicone materials, and hair care compositions comprising such materials, are suitable for protecting hair and/or reducing hair damage upon treatment by heat because they do not evaporate when subject to high temperature and they do not also decompose and/or form by-products. It is believed, therefore, that the heat-stable silicone material—particularly the polydimethylsiloxane (P) described below—remains of hair fibers after applying of the hair care composition and limits the impact of the heat onto hair fibers.

The process, according to the present invention comprises the step of providing a hair care composition comprising a heat-stable silicone material and a cosmetically acceptable carrier.

As used herein, the expression "heat-stable silicone material" means a silicone material which is stable even at high temperatures. As used herein, the expression "high temperature" means temperature up to 300° C., preferably temperature up to 280° C., more preferably temperature up to 250° C. As used herein, the expression "stable" means that the silicone material does not decompose and/or does not form by-products and/or does not evaporate when heated up to high temperature. Particularly, when a heat-stable silicone material is applied onto a substrate, e.g. hair fibres, the expression "stable" means that the silicone material remains on said substrate without evaporating. Heat-stability of silicone material may be accessed using the Thermogravimetric analysis, particularly using the apparatus TG 209, manufactured from Netsch.

Preferably, the heat-silicone material is a heat-stable polydimethylsiloxane.

More preferable, the heat-stable polysiloxane is a polydimethylsiloxane (P) having aminoalkyl groups and having an amine number of at least 0.1 meq/g of polydimethylsiloxane (P), and comprising units of the formula I $$R^1_a R^2_b SiO_{(4-a-b)/2} \quad (I),$$

in which $R^1$ are optionally halogen-substituted alkyl radicals having 1-40 carbon atoms, or are —OR or —OH radicals;

R are optionally halogen-substituted alkyl radicals having 1-40 carbon atoms;

$R^2$ are aminoalkyl radicals of the formula II $$—R^3—NR^4R^5 \quad (II);$$

$R^3$ are divalent hydrocarbon radicals having 1-40 carbon atoms;

$R^4$ are monovalent hydrocarbon radicals having 1-40 carbon atoms or are H;

$R^5$ is a radical of the formula III $$—(R^6—NR^4)_x R^4 \quad (III);$$

$R^6$ is a divalent radical of the formula IV $$—(CR^4R^4—)_y \quad (IV);$$

x is 0 or a value from 1 to 40; y is 1 or 2; a is 0, 1, 2 or 3; b is 0, 1, 2 or 3; and, a+b on average is from 1.5 to 2.5;

not more than 9 mol % of the radical $R^1$ being OH or OR.

The alkyl radicals $R^1$ and R may be linear, cyclic, branched, saturated or unsaturated. The alkyl radicals $R^1$ and R preferably have 1-18 carbon atoms, in particular 1-6 carbon atoms, and the methyl radical or ethyl radical is particularly preferred. Preferred halogen substituents are fluorine and chlorine. Particularly preferred radicals $R^1$ are the methyl radical, methoxy radical, ethoxy radical or —OH.

The divalent hydrocarbon radicals $R^3$ may be halogen-substituted, linear, cyclic, branched, aromatic, saturated or unsaturated. The radicals $R^3$ preferably have 1 to 6 carbon atoms, and alkylene radicals are particularly preferred, in particular propylene. Preferred halogen substituents are fluorine and chlorine.

The monovalent hydrocarbon radicals $R^4$ may be halogen-substituted, linear, cyclic, branched, aromatic, saturated or unsaturated. The radicals $R^4$ preferably have 1 to 6 carbon atoms, and alkyl radicals are particularly preferred. Preferred halogen substituents are fluorine and chlorine. Particularly preferred substituents $R^4$ are methyl, ethyl, cyclohexyl and H.

In the polydimethylsiloxanes, b preferably has the value 0 or 1, and a+b preferably has an average value of from 1.9 to 2.2. In the polydimethylsiloxanes, x is preferably 0 or a value from 1 to 18, most preferably from 1 to 6.

Particularly preferred radicals $R^2$ are —$CH_2N(R^4)_2$, —$(CH_2)_3N(R^4)_2$ and —$(CH_2)_3N(R^4)(CH_2)_2N(R^4)_2$.

The polydimethylsiloxane (P) is composed of at least 3, in particular at least 10, units of the general formula (I).

The ratio of a to b is chosen so that the polydimethylsiloxane (P) has an amine number of at least 0.1 meq/g of polydimethylsiloxane (P), preferably at least 0.6 meq/g of polydimethylsiloxane (P). The amine number of the polydimethylsiloxane (P) is preferably not more than 7 meq/g of polydimethylsiloxane (P).

The viscosity of the polydimethylsiloxane (P) is preferably from 1 to 100,000 mPa·s, in particular from 10 to 10,000 mPa·s, at 25° C.

Said composition may comprise from 0.001% to 50%, preferably from 0.01% to 30%, more preferably from 0.1% to 20%, still more preferably from 0.1% to 5%, polydimethylsiloxane (P) by total weight of the hair treating composition.

The polydimethylsiloxanes (P) and emulsions or dispersions thereof are described in US 2006/0041026 A1 which is hereby incorporated by reference. An oil-in-water emulsion of polydimethylsiloxanes (P) suitable for the invention is sold under the trademark Wacker® HC 303 VP by Wacker-Chemie AG (Germany).

In a preferred embodiment, the composition is an emulsion and contains a MQ silicone resin. The MQ silicone resin preferably contains at least 80 mol %, preferably at least 95 mol %, of units of the general formulae (V) and (VI):

$$R^7_3 SiO_{1/2} \quad (V),$$

$$SiO_{4/2} \quad (VI),$$

in which $R^7$ are optionally halogen-substituted hydrocarbon radicals having 1-40 carbon atoms or H, —OR or —OH radicals, and the ratio of the units of the general formulae (V) and (VI) is from 0.5 to 2.0, preferably from 0.5 to 1.5, and not more than 3% by weight, preferably not more than 2.5% by weight, of the radicals $R^7$ are —OR and —OH.

The remaining units of the MQ silicone resin are preferably units of the general formulae (VII) and (VIII):

$$R^7_2 SiO_{2/2} \quad (VII),$$

$$R^7 SiO_{3/2} \quad (VIII),$$

The monovalent hydrocarbon radicals $R^7$ may be halogen-substituted, linear, cyclic, branched, aromatic, saturated or unsaturated. The radicals $R^7$ preferably have 1 to 6 carbon atoms, and alkyl radicals and phenyl radicals are particularly preferred. Further halogen substituents are fluorine and chlorine. Particularly preferred substituents $R^7$ are methyl, ethyl, phenyl and H. The emulsions preferably contain from 1 to 200 parts by weight, particularly preferably from 5 to 100 parts by weight, of MQ silicone resin.

The hair care composition may further comprise a protonating agent. The protonating agent may be a monoprotic or polyprotic acid, water-soluble or water-insoluble acid, and/or an organic or inorganic acid. Preferably, the protonating agent is selected from formic acid, acetic acid, sulfuric acid, hydrochloric acid, citric acid or mixtures thereof. Preferably, the protonating agent is added in an amount of from 0.05 to 2 mol of acidic proton per mole of basic nitrogen atom of the radicals $R^2$.

The above polydimethylsiloxane (P) in combination with the protonating agent can advantageously be used for manufacturing a cosmetic composition for treating human hair.

By treating hair with said polydimethylsiloxane (P) together with the protonating agent the treated hair becomes water repellent. This allows to use said polydimethylsiloxane (P) and the protonating agent for reducing the drying time of human hair. This also allows using said polydimethylsiloxane (P) and the protonating agent, and hair care compositions comprising these components, for reducing the drying time of human hair.

Providing a hair care composition allowing the reduction of the drying time is particularly useful in processes according to the present invention. Indeed, such composition allows the reduction of the time needed when treating hair using the heat generating hair care appliance and, therefore, it contributes further to the protection of hair and/or reduction of hair damage upon treatment of hair by heat.

The hair care composition also comprises a cosmetically acceptable carrier. The cosmetically acceptable carrier may be any carrier suitable for formulating the heat-stable silicone material into a composition being suitable for application onto hair. The cosmetically acceptable carrier may be selected from either an aqueous medium or an aqueous-alcoholic medium. When the carrier is an aqueous-alcoholic carrier, this carrier comprises water and an alcohol. When the carrier is an aqueous carrier, this carrier consists essentially of water and is substantially free of alcohol. Said composition may comprise from 0.1% to 99%, preferably from 1% to 99%, more preferably from 10% to 99%, still more preferably from 30% to 99%, water by weight of the total composition.

The hair care composition may be in the form of an emulsion, a solution, a dispersion, or any other form suitable for application onto hair. When being in the form of an emulsion, said emulsion may be a water-in-oil emulsion, an oil-in-water emulsion, or a multiple emulsion.

The hair care composition may be a leave-in composition or a rinse-off composition.

The hair care composition may be selected from a shampoo; a hair-conditioning composition; a hairstyling composition; or combinations thereof. When being a hairstyling composition, said composition may be a gel composition; a spraygel composition, optionally dispensed using a mechanical spray device and/or at least one propellant; a non-aerosol hairspray, optionally dispensed using a suitable mechanically operated spraying device; a foamable composition, optionally dispensed using devices for foaming; hair wax composition; hair lotion composition; hair cream composition; or combinations thereof.

The hair care composition may be applied on wet hair and/or on dry hair.

The hair care composition may further comprise at least one cosmetic hair treatment agent selected from hairstyling polymers, hair-conditioning agents, hair-cleaning agents, or mixtures thereof.

The hair care composition may comprise any suitable and conventional hair styling polymers. Particularly, the hairstyling polymer may be selected from nonionic hair styling polymer, anionic hair styling polymer, zwitterionic and/or amphoretic hairstyling polymer, cationic hair styling polymer, or mixtures thereof. Suitable hairstyling polymers may be found in the CTFA International Cosmetics Ingredient Dictionary and Handbook, "Hair Fixatives", 12$^{th}$ edition (2008). Suitable hairstyling polymers are, for example, those materials disclosed from page 12, line 5 to page 19, line 1 of the European patent application 08151246.9 filed on 11 Feb. 2008, which is incorporated herewith by reference.

The hair care composition may comprise from 0.01% to 10% by weight, preferably from 0.1% to 8%, more preferably from 0.1% to 5%, hairstyling polymer by total weight of the composition.

Nonionic hairstyling polymers may be natural or synthetic polymers. Suitable nonionic hair styling polymers may be polymers obtained from polymerization of at least one type of monomers selected from vinylpyrrolidone; vinylcaprolactam; vinyl esters; vinyl alcohol; vinyl acetate; (meth) acrylamide, and/or its derivatives; (meth)acrylic acid, its salts, and/or its derivatives; propylene and/or ethylene glycol acid; crotonic acid; or mixtures thereof. For example, such polymers are available under the tradenames Luviskol® or Luviset Clear®.

Suitable anionic hairstyling polymers may be selected from acrylic acid/alkyl acrylate/N-alkylacrylamide terpolymer; vinyl acetate/crotonic acid copolymer; C1-C5-alkyl acrylate/(meth)acrylic acid copolymer; sodium polystyrenesulfonate; vinyl acetate/crotonic acid/vinyl alkanoate copolymer; vinyl acetate/crotonic acid/vinyl neodecanoate copolymer; aminomethylpropanol acrylate copolymer; vinylpyrrolidone/(meth)acrylic copolymer; methyl vinyl ether/maleic monoalkyl esters copolymer; aminomethylpropanol salts of allyl methacrylate/(meth)acrylate copolymer; ethyl acrylate/methacrylic acid copolymer; vinyl acetate/ mono-n-butyl maleate/isobornyl acrylate copolymer; octylacrylamid/(meth)acrylic acid copolymer; polyesters of diglycol, cyclohexanedimethanol, isophthalic acid and sulfoisophthalic acid; or mixtures thereof.

Suitable zwitterionic or amphoteric hairstyling polymers may be selected from alkylacrylamide/alkylaminoalkyl methacrylate/(meth)acrylic acid copolymers; copolymers which are formed from at least one first monomer type which has quaternary amine groups, and at least one second monomer type which has acid groups; copolymers of fatty alcohol acrylates, of alkylamine oxide methacrylate and at least one monomer chosen from acrylic acid and methacrylic acid; methacryloylethylbetaine/methacrylic acid and/or esters copolymers; polyquaternium-47; polyquaternium-43; oligomers or polymers, preparable from quaternary croton betaines or quaternary croton betaine esters; or mixtures thereof.

Suitable cationic hairstyling polymers may be selected from homopolymers or copolymers, where the quaternary nitrogen groups are present either in the polymer chain or as substituent on one or more of the monomers. The monomers containing ammonium groups may be copolymerized with noncationic monomers. Suitable cationic monomers may be unsaturated, free-radically polymerizable compounds which carry at least one cationic group, in particular ammonium-substituted vinyl monomers, such as, for example, trialkylmeth-acryloxyalkylammonium, trialkylacryloxyalkylammonium, dialkyldiallylammonium and quaternary vinylammonium monomers with cyclic, cationic nitrogen-containing groups, such as pyridinium, imidazolium or quaternary pyrrolidones, e.g. alkylvinylimidazolium, alkylvinyl-pyridinium, or alkylvinylpyrrolidone salts. The alkyl groups of these monomers are preferably lower alkyl groups, such as, for example, C1- to C7-alkyl groups, particularly preferably C1- to C3-alkyl groups. Suitable noncationic monomers may be selected from (meth)acrylamide, derivatives thereof; acrylate, its derivative thereof; vinylcaprolactone, vinylcaprolactam, vinylpyrrolidone, vinyl esters, vinyl alcohol, propylene glycol or ethylene glycol. For example, suitable cationic hairstyling polymers are available under the tradenames Gafquat® 755 N; Gafquat® 734; Gafquat® HS 100; Luviquat® HM 550; Merquat® Plus 3300; Gaffix® VC 713; Aquaflex® SF 40.

Cationic hairstyling polymers may also be derived from natural polymers, preferably natural polymers selected from cationic derivatives polysaccharides such as cellulose, starch and/or guar; chitosan, its salts, and/or its derivatives; or mixtures thereof. For example, suitable conventional polymers are polyquaternium-4; polyquaternium-10; polyquaternium-24; guar hydroxypropyltrimonium chloride; chitosonium pyrrolidonecarboxylate.

The hair care composition may further comprise any suitable and conventional hair-conditioning agents. The term "hair conditioning agent" means herewith any cosmetically acceptable compound having a cosmetic effect on hair, such as providing gloss to hair, making hair more manageable, improving hair touch, improving combability and/or giving hair more volume. Suitable hair-conditioning agents may be found in the CTFA International Cosmetics Ingredient Dictionary and Handbook, "Hair conditioning agents", 12$^{th}$ edition (2008). Hair conditioning agent may be selected from cationic surfactant, nonionic surfactant, silicone-conditioning agent, organic oily conditioning agent, or mixtures thereof. Suitable hair-conditioning agents are, for example, those materials disclosed from page 19, line 3 to page 27, line 33 of the European patent application 08151246.9 filed on 11 Feb. 2008, which is incorporated herewith by reference.

Suitable cationic surfactants contain preferably amino or quaternary ammonium moieties. For example, cationic surfactant may be surfactants of formula

[NR4,R5,R6,R7]$^+$.X$^-$ wherein R4 to R7 are independently an aliphatic group of from 1 to 22 carbon atoms; an aromatic, alkoxy, polyoxyalkylene, alkylamido, hydroxyalkyl, aryl or alkylaryl group having from 1 to 22 carbon atoms; and X$^-$ is a salt-forming anion. Suitable cationic surfactants may be selected from cetyl trimethyl ammonium salts; behenyl trimethyl ammonium salts; dimethyl ditallow ammonium salts; stearyl amidopropyl dimethylamine; (di)esterquats; quaternium 8, 14, 15, 18, 22, 24, 26, 27, 30, 33, 37, 53, 60, 61, 72, 78, 80, 81, 82, 83, 84, and/or 91; or mixtures thereof.

Suitable nonionic surfactants may be surfactants having a HLB of less than 8. Suitable nonionic surfactants may be selected from glyceryl esters; sugar esters; alkylpolyglucoside ethers; oleyl- or isostearylpolyglucoside; polyoxyethylene (20) sorbitan monostearate; or mixtures thereof.

Suitable silicone conditioning agents may be volatile or nonvolatile, and/or soluble or insoluble silicones. For example, suitable silicone conditioning agents are available under the tradenames SF 1075 methyl phenyl fluid (Electric company); DC200 Fluid, DC244, DC245, DC345, DC556 Cosmetic Grade Fluid, DC1248 (Dow Corning).

Suitable organic oily conditioning agents may be nonvolatile, water insoluble, organic, oil or fat. Organic oily conditioning agents may be selected from hydrocarbon oils and fatty esters.

Suitable fatty alcohols may be nonvolatile low melting point fatty alcohol.

A variety of additional optional ingredients may be incorporated into the composition of the present invention. Non-limiting examples of these additional ingredients may be selected from preservatives; antioxidants; sequestering agents; solvents; fragrances & perfumes; fillers; screening agents; odor absorbers; coloring materials; lipid vesicles; detersive surfactants; thickening agents and suspending agents; viscosity modifiers; pearlescent aids; UV-filters and sunscreens; agents for combating free radicals; polyvinyl alcohol; pH adjusting agents; salts; coloring agents; polymer plasticizing agents; direct dyes; or mixtures thereof.

The hair care composition may further comprise at least one direct hair dyes. Said composition may comprise from 0.01% to 15%, preferably from 0.1% to 10%, more preferably from 0.5% to 8%, direct hair dyes by weight of the total composition.

The hair care composition may further comprise at least one viscosity-modifying substance. Said composition may comprise from 0.01% to 20%, preferably from 0.05% to 10%, more preferably from 0.1% to 5%, viscosity-modifying substance by weight of the total composition.

The hair care composition may further comprise at least one emulsifier and/or surfactant not being a hair conditioning agent. Said emulsifier and/or surfactant may be selected from nonionic surfactants; anionic surfactants; amphoretic surfactants; or mixtures thereof. Said composition may comprise from 0.01% to 50%, preferably from 0.05% to 20%, more preferably from 0.1% to 15%, emulsifier and/or surfactant by weight of the total composition.

The hair care composition may further comprise at least one pigment. The pigment may be selected from natural pigments; synthetic pigments; or mixture thereof. The pigments may be selected from organic pigment, inorganic pigment; or mixtures thereof. The pigments may be selected from colored pigments; pearlescent pigments; or mixtures thereof. Said composition may comprise from 0.01% to 25%, preferably from 5% to 15%, pigment present in the product mass in undissolved form by weight of the total composition.

The hair care composition may further comprise at least one particulate substance. Particulate substance may be selected from silica; silicates; aluminates; clay earths; mica; insoluble salts, particularly insoluble inorganic metal salts; metal oxides; minerals; insoluble polymer particles; or mixtures thereof. Said hair care composition may comprise from 0.01% to 10%, preferably from 0.05% to 5%, of at least one particulate substance by weight of the total composition.

The hair care composition may further comprise at least one photoprotective substance. Said composition may comprise from 0.01% to 10%, preferably from 0.1% to 5%, more preferably from 0.2% to 2%, photoprotective substance by weight of the total composition.

The hair care composition may further comprise at least one preservative. Said composition may comprise from 0.01% to 5% by weight, more preferably from 0.05% to 1%, of at least one preservative by weight of the total composition.

The hair care composition may have a viscosity at 25° C. from 0.1 mPa·s to 1,000,000 mPas, preferably from 1 mPa·s to 80,000 mPa·s, more preferably from 5 mPa·s to 3,500 mPa·s. The viscosity may be measured—if not otherwise defined—by HAAKE Rotation Viscometer VT 550 with cooling/heating vessel and sensor systems according to DIN 53019 (MV-DIN, SV-DIN), shear rate is 12.9 s$^{-1}$.

The hair care composition may have a pH value from 2.0 to 12.0, preferably from 3.0 to 9.0, more preferably from 4.5 to 7.5. In order to achieve a specific pH, said composition may further comprise an alkalizing agent and/or an agent for adjusting the pH value.

In a preferred embodiment, the process comprises the steps of providing and applying a hair care composition comprising at least one heat stable silicone material, at least one volatile component above 100° C. and a cosmetically acceptable carrier. Preferably, said composition consists essentially of at least one heat stable silicone material, at least one volatile component above 100° C. and a cosmetically acceptable carrier. More preferably, said composition is substantially free of heat-unstable component.

As used herein "volatile above 100° C." means that the component evaporates above 100° C. and that, when applied onto a substrate such as hair fibers, the component leaves no residue and/or by-products onto said substrate. Common volatile components above 100° C. are water and alcohols.

As used herein, the expression "heat-unstable" means that a component does not evaporate fully when subject to high temperatures and, when applied onto a substrate such as hair, leaves by-products that may alter the structure of hair fibers and/or induce hair damage when heated up at high temperatures.

The process, according to the present invention, also comprises the step of applying onto hair a sufficient amount of hair care composition for treating hair. As used herein, the expression "sufficient amount of hair care composition for treating hair" means preferably the application from 0.01 g to 5 g of hair care composition for 1 g of hair. The composition may be applied onto hair by dispending it directly onto hair and then rubbing hair to distribute this composition evenly onto hair. Alternatively, the composition may be dispensed into the hand palm and/or onto any suitable substrate and then rubbing hair with the hand and/or said substrate to apply and distribute this composition evenly onto hair.

The process, according to the present invention, also comprises the steps of providing a heat generating hair care appliance and then treating hair using this appliance for a sufficient amount of time. As used herein, the expression "sufficient amount of time" means preferably from 1 min to 2 h, more preferably from 1 min to 1 h, still more preferably from 1 min to 20 min Heat generating hair care appliances fall into two major categories, i.e. appliances to be used typically on wet hair and appliances to be used typically on dry hair.

Appliances to be used preferably on wet hair are referred herein as to "hot air hair care appliances". For example, hot air hair care appliances may be hair dryers and/or hot air hair stylers. A hair dryer, for example, directs hot air towards the hair, as to dry it. The air is typically directed through appropriate orifices and accelerated by a fan. The hair may be heated by a resistive heater. Such hair dryers may also take the form of drying hoods, where a major portion of the head is covered by some form of hood. Hairdryer distances are typically down to 10 cm. Hot air stylers direct hot air through some sort of attachment for combing or otherwise treating the hair. A hot air hair styler is typically used such that the respective appliance touches the hair and hence the styler itself is used in the vicinity of the hair (for example at a distance of 5 or 10 or 20 centimeters). A conventional hot air dryer is used in a somewhat larger distance to the hair (for example at a distance of 20 or 30 or 40 centimeters) and often is used with the aide of a comb or a brush. The devices of the first group deliver hot air at a temperature from 50 to about 100° C. Some devices may deliver hot air temperatures up to 130° C., but no common device produces air hotter than 150° C.

Appliances to be used typically on dry hair are referred herein as to "hot surface hair care appliances". For examples, hot surface hair care appliances may be hair curlers and hair straighteners. They also typically rely on resistive heating, but heat is not transported through hot air, but by direct contact with the hair. The transfer is often made by bringing the hair in contact with some metal or ceramic surface of the appliance. These devices are not or at least not primarily used to dry the hair. Rather are they used to change the hair style, typically either to create curls or to straighten hair. The surfaces meant for hair contact of these devices typically reach temperatures from 130° C. to 250° C. Most devices have hair contact surfaces with temperatures from 200° C. to 230° C.

U.S. Pat. No. 5,612,849 and U.S. Pat. No. 6,191,930 disclose a heat generating hair care appliance in the form of a hot air hair care appliance. The respective devices are typically referred to as hair dryers or blow dryers. US D383245 discloses another heat generating hair care appliance in the form of a hot air hair care appliance. The respective devices are typically referred to as hot air stylers or hair stylers. US 2008/0196739 discloses a heat generating hair care appliance in the form of a hot surface hair care appliance. The respective device is typically referred to as a hair straightener.

In a preferred embodiment, the process comprises the steps of providing a heat generating hair care appliance being a hot air hair care appliance, and then treating hair at a temperature ranging from 20° C. to 150° C. using said appliance for a sufficient amount of time for drying and/or styling hair. The hot air hair care appliance is preferably selected from hair dryer and/or hot air hair styler. When said appliance is a hair dryer, hair are preferably treated at a temperature ranging from 20° C. to 110° C. When said appliance is a hot air hair styler, hair are preferably treated at a temperature ranging from 50° C. to 150° C.

In another preferred embodiment, the process comprises the steps of providing a heat generating hair care appliance being a hot surface hair care appliance, and then treating hair at a temperature ranging from 90° C. to 250° C. using said appliance for a sufficient amount of time for drying and/or styling hair. The hot surface hair care appliance is preferably selected from hair curlers and hair straigtheners. When said appliance is a hair curler, hair are preferably treated at a temperature ranging from 90° C. to 200° C. When said appliance is a hair straigthener, hair are preferably treated at a temperature ranging from 90° C. to 250° C.

In an alternative embodiment, the process comprises the steps of providing a heat generating at least two hair care appliances being a hot air hair care appliance and a hot surface hair care appliance, and then treating successively hair using the hot air hair care appliance and then the hot surface hair care appliance.

The hair care composition is preferably applied onto hair before treating hair using said appliance. This composition is applied onto hair preferably from 1 min to 2 h, more preferably from 1 min to 1 h, still more preferably from 1 min to 20 min, before treating hair using said appliance.

The process, according to the present invention, may further comprise the step of wetting hair before, during and/or after applying the hair care composition onto hair. This step may be performed using an aqueous composition and/or water.

The process, according to the present invention, may also further comprise the step of rinsing off the hair care composition comprising the heat-stable silicone material. It may be used water and/or any suitable rinsing composition. Rinsing-off the hair care composition is preferred when said composition is a shampoo and/or a rinse-off hair-conditioning composition. This step of rinsing off the hair care composition is preferably performed from 30 sec to 20 min, more preferably from 30 sec to 5 min after applying the hair care composition. This step of rinsing off the hair care composition is also preferably performed before treating hair using the heat generating hair care appliance.

The process, according to the present invention, may also further comprise the step of drying hair by toweling hair and/or by pressing hair with hands. This step may be useful to remove the excess of water. The step is preferably conducted after applying the hair care composition onto hair and before treating hair using a heat generating hair care appliance.

The process, according to the present invention, may also further comprise the step of combing and/or brushing hair. This step may be performed before and/or after treating hair using a heat generating hair care appliance.

In a preferred embodiment, the present invention relates to a process for reducing hair damage upon treatment of hair by heat comprising the steps of:

providing a hair care composition comprising a heat-stable polydimethylsiloxane (P);
applying from 0.01 g to 5 g/g hair of said composition onto hair;
optionally, wetting hair with an aqueous composition before, during and/or after applying said hair care composition onto hair;
optionally, rinsing off said hair care composition;
optionally, drying hair by toweling and/or pressing hair with hands in order to remove the excess of water;
providing two heat generating hair care appliances being a hot air hair care appliance and a hot surface hair care appliance;
treating hair using the hot air hair care appliance from 1 min to 20 min for substantially drying hair;
then treating hair using the hot surface hair care appliance from 1 min to 20 min for styling hair;
optionally, combing and/or brushing hair before, during and/or after treating hair with the heat generating hair care appliances.

According to a second aspect, the present invention relates to the use of a hair care composition, as defined above, for protecting hair and reducing hair damage upon treatment of hair by heat. In a preferred embodiment, the present invention relates to the use of said hair care composition for protecting hair and reducing hair damage upon treatment of hair by hot air hair care surface. In another embodiment, the present invention relates to the use of said hair care composition for protecting hair and reducing hair damage upon treatment of hair by hot surface hair care surface.

It is indeed particularly advantageous using a hair care composition comprising a heat-stable silicone material—e.g. a heat-stable polydimethylsiloxane such as polydimethylsiloxane (P) of the type present in the material Wacker HC 303—in order to protect hair against hair treatments by heat and in order to reduce, or even prevent, hair damages induced by hair treatments by heat. Heat-stable silicone materials are useful for protecting hair and/or reducing hair damage upon treatment of hair by heat as it is believed that these materials—particularly polydimethylsiloxane (P) described below—remain of hair fibers after applying of the hair care composition incorporating them and limit the impact of the heat onto hair fibers.

According to a third aspect, the present invention relates to the use of a heat-stable silicone material, as defined above, for preparing a heat-stable hair care composition. As used herein, the expression "heat-stable hair care composition" means that the hair care composition comprises at least one component being heat stable, i.e. at least one component which does not decompose and/or does not form by-products and/or doe not evaporate when heated up to high temperatures, typically up to 300° C.

In contrast, the heat-stable hair care composition may comprise further components not being heat stable. Typically, said composition may comprise components that would evaporate when subject to high temperatures, preferably when subjected to a temperature of 100° C. or above. One common component evaporating when subjected to a temperature of 100° C. or above is water.

According to a fourth aspect, the present invention relates a kit for reducing hair damage upon treatment of hair by heat comprising:
a hair care composition—according to the first aspect of the invention—comprising a heat-stable silicone material and a cosmetically acceptable carrier;
a heat-generating hair care appliance—according to the first aspect of the invention—, preferably a hot air hair care appliance and/or a hot surface hair care appliance.

The following examples further describe and demonstrate the preferred embodiments within the scope of the present invention. The examples are given solely for the purpose of illustration, and are not to be construed as limitations of the present invention since many variations thereof are possible without departing from its scope.

All weights provided in these examples are weights of the commercially available materials, including active(s) and/or solvent and/or by-products.

Evaluation of the function stability of the silicone material over the whole range of styling up to 300° C.

The thermogravimetric analysis—designated thereafter as "TGA"—was conducted using the device TG 209 manufactured by Netsch.

The composition to be tested comprised 20% Wacker HC 303 material (emulsion comprising polydimethylsiloxane (P)) and water (qsp). Specifically, the composition comprised 5% (active) polydimethylsiloxane (P).

A sample of the composition to be tested was loaded onto the apparatus.

The sample was evaporated with a thermo balance in an $Al_2O_3$ melting point in the temperature range from 20° C. to 300° C. with a heating rate of 20K/min including two isothermal steps at 250° C. and 300° C. each for 10 min.

The residues in the temperature range from 100° C. to 300° C. in Thermogravimetric analysis is shown in the table below.

| | Residues in percentage | | | | | |
|---|---|---|---|---|---|---|
| | 100° C. | 150° C. | 170° C. | 200° C. | 250° C. | 300° C. |
| Sample | 57 | 6 | 5 | 5 | 5 | 5 |

The above data shows that 94% of the volatile substances, mainly water, in the composition tested were already evaporated at 150° C. and a stabile mass of 5% was left in the following temperature steps. These data demonstrated that the remaining substance after heating the sample up to 300° C. is polydimethylsiloxane (P) of Wacker HC303, and that said polymethylsiloxane is stable at high temperature, i.e. does not decompose and/or does not form by-products and/or does not evaporate when heated up to high temperature.

Such data demonstrate the suitability of application of polydimethylsiloxane (P) on hair before treatment of hair by heat, because of its stability at high temperature.

Compositions Suitable for Use in the Processes According to the Present Invention All compositions exemplified below comprise amino-functional organopolysiloxanes prepared as follows:

The amino-functional organopolysiloxanes used are as follows:
Amine Oil 1: Amine Oil 1 has a viscosity of about 1000 $mm^2$/s at 25° C., the functional radicals are —$CH_2$)$_3$NH($CH_2$)$_2$NH$_2$ and has an amine number of 0.6 meq/g of organopolysiloxane. In addition, the organopolysiloxane contains about 0.75 mol % of reactive OMe/OH radicals as terminal groups.

Amine Oil 2: Amine Oil 2 has a viscosity of about 1000 mm$^2$/s at 25° C., the functional radicals are —CH$_2$)$_3$NH(CH$_2$)$_2$NH$_2$ and has an amine number of 0.6 meq/g of organopolysiloxane. The terminal groups in this case are Me$_3$SiO radicals.

Amine Oil 3: Amine oil 3 has a viscosity of about 230 mm$^2$/s at 25° C., the functional radicals are —CH$_2$)$_3$NH(CH$_2$)$_2$NH$_2$, and an amine number of 2.6 meq/g of organopolysiloxane. The terminal groups are likewise Me$_3$SiO radicals. Said amino-functional organopolysiloxanes are formulated as emulsions as follows:

Emulsion A: 16.g of Amine Oil 1 are added to 6 g of water, 6 g of ethylene glycol monobutyl ether and 0.17 g of acetic acid at room temperature while stirring, and the remaining water to a total weight of 100 g is then also incorporated. A milky opaque emulsion is obtained. The emulsion is added at room temperature as last ingredient to the active solution/dispersion of the following examples.

Emulsion B: 16.g of a mixture of 11.1 g of Amine Oil 2 and 4.9 g of MQ resin are added to 6 g of water, 6 g of ethylene glycol monobutyl ether and 0.17 g of acetic acid at room temperature while stirring, and the remaining water to a total weight of 100 g is then also incorporated. A milky opaque emulsion is obtained. The emulsion is added at room temperature as last ingredient to the active solution/dispersion of the following examples.

Emulsion C: 16.g of a mixture of 11.1 g of Amine Oil 3 and 4.9 g of MQ resin are added to 6 g of water and 0.17 g of acetic acid at room temperature while stirring, and the remaining water to a total weight of 100 g is then also incorporated. A milky opaque emulsion is obtained. The emulsion is added at room temperature as last ingredient to the active solution/dispersion of the following examples.

The hair care compositions described hereafter and comprising either emulsion A, emulsion B or emulsion C, are prepared using conventional mixing methods. These formulations are suitable for use in the processes according to the present invention.

Liquid gel comprising 2.00 g Emulsion A; 1.00 g Luviset® Clear, 1.50 g Surfactant 193, 0.30 g Carbomer, 0.30 g AMP 95%, 0.20 g Emulgin L, 0.15 g perfume, 0.40 g Natrosol® G, 16.50 g Ethanol, qsp 100.00 g water with water.

Rapid Drying Gel comprising 2.90 g Emulsion B, 1.00 g Luviset® Clear, 1.80 g Polyvinylpyrrolidone K 90; 1.00 g Direct dye; 1.50 g Surfactant 193; 1.00 g Synthalen® W 2000; 0.30 g AMP 95%; 0.30 g PEG-25 PABA (Uvinul® P 25); 0.15 g Panthenol; 0.30 g Perfume; 34.20 g Ethanol; 0.10 g Keratin hydrolysate; qsp 100.00 g with water.

Pump-setting foam comprising 1.20 g Emulsion C, 1.80 g Luviset® Clear, 1.90 g Direct dye, 0.40 g Cocamidopropyl Hydroxysultaine, 0.10 g Rosemary leaf extract (Extrapon® Rosemary), 8.90 g ethanol, 0.10 g Extrapon® seven herbs-extract, 0.10 g Panthenyl ethyl ether, 0.15 g Perfume, qsp 100.00 g with water. The composition is packaged in a packaging with mechanically operated pump foaming device.

Aerosol-setting foam-extra strong hold comprising 1.20 g Emulsion A, 2.10 g Luviset® Clear, 0.60 g Vinyl acetate/crotonic acid copolymer, 0.50 g Polyquaternium-7, 4.00 g Butane, 4.00 g Propane, 8.90 g Ethanol 510, 0.40 g PEG-25 PABA, 0.20 g Panthenol, 0.20 g Perfume, 0.20 g Laureth-4, 0.07 g C9-C11 Pareth-8, qsp 10.00 g with water. The composition is bottled in an aerosol can with foaming head.

Setting spray comprising 2.20 g Emulsion B, 1.00 g Luviset® Clear, 0.65 g Octylacrylamide/Acrylates/Butylaminoethylmethacrylate Copolymer (Amphomer®), 0.20 g Celquat® L200, 28.5 g Ethanol, 0.60 g Aminomethylpropanol 95%, 0.25 g Perfume, 0.20 g Cetyltrimethylammonium chloride, qsp 60.00 g water. The composition is bottled in a packaging with pump spray device.

Rinse out Conditioner comprising 3.00 g Emulsion A, 1.00 g cetyltrimethyl ammonium chloride, 1.00 g polymethylphenyl siloxane, 0.40 g phenoxy ethanol, 0.20 g PHB-methylester, 1.00 g Dow Corning 949 Cationic Emulsion®, 5.00 g isododecane, 0.40 g perfume oil, qsp 100.00 g Water.

Leave in Conditioner comprising 1.80 g Emulsion C, 0.10 g vitamine E-acetate, 0.50 g polymethylphenyl siloxane, 10.00 g propylene glycol, 0.50 g behenyl trimethylammonium chloride, 0.05 g sodium chloride, 0.30 g d-panthenol, 0.30 g PHB-propylester, 2.00 g isododecane, 0.20 g perfume oil, qsp 100.00 g water.

Shampoo comprising 0.20 g Jaguar C-162, 40.00 g sodium laureth sulfate (LES 28%), 5.00 g Cocamidopropyl betaine, 2.00 g Dow Corning 200 Fluid/350 CS, 0.15 g Perfume, 6.00 g Emulsion C, qsp 100.00 g Water The tradenames/raw materials used in the examples are Abilquat® 3270 (Quaternium-80, 50% in propylene glycol) from Goldschmidt; Aculyn® 48 (PEG-150/stearyl alcohol/SMDI copolymer, 19% in water) from Rohm and Haas; AMP 95% (aminomethylpropanol, 95% aqueous solution); Amphomer® (octylacrylamide/acrylates/butylaminoethylmethacrylate copolymer); Aristoflex® AVC (Ammonium Acryloyldimethyltaurate/VP copolymer); Aquaflex® FX-64 (isobutylene/ethylmaleimide/hydroxyethylmaleimide copolymer, 40% strength in water/ethanol) from ISP; Aquaflex® SF 40 (VP/vinyl caprolactam//DMAPA acrylates copolymer, 40% in ethanol) from ISP; Advantage® S (vinyl caprolactam/VP/dimethylaminoethyl methacrylate copolymer); Carbomer—Carbopol (acrylic acid homopolymer); Celquat® L200 (copolymer of hydroxyethylcellulose and diallyldimethylammonium chloride; Polyquaternium-4); GENAMIN CTAC 50 (cetrimonium chloride; cetyltrimethylammonium chloride); Copolymer 845 (VP/Ddimethylaminoethylmethacrylate copolymer, 20% in water) from ISP; Dehydol® LS 4 (Lauryl alcohol tetraoxyethylen ether); Dekaben® LMB (iodopropynyl butylcarbamate, 10% strength in butylene glycol); Dekaben® LMP (Phenoxyethanol and iodopropynyl butylcarbamate); Diaformer Z-711 (acrylates/lauryl acrylate/stearyl acrylate/ethylamine oxide methacrylate copolymer, 40%) from Clariant; Dow Corning 1401 (High molecular weight Dimethiconol, 13% in cyclomethicone); Eumulgin® L (PEG-1-PEG-9 lauryl glycol ether; Flexan® (Sodium polystyrenesulfonate); GAFQUAT® 755 N (Polyquaternium-11); Jaguar C-17/162 (guar hydroxylpropyltrimonium chloride) Laureth-4 (Lauryl alcohol tetraoxyethylen ether); Luviset® Clear (Terpolymer of vinylpyrrolidone, methacrylamide and vinylimidazole) from BASF; Luviskol® VA 64 (vinylpyrrolidone/vinylacetate copolymer); Luviskol® K 90 Powder (vinylpyrrolidone); Luvimer® 100 P (t-butyl acrylate/ethyl acrylate/methacrylic acid copolymer); Natrosol® G (hydroxyethylcellulose); Pemulen® (acrylates/C10-30 alkyl acrylate crosspolymer); Structure® 3001 (acrylates/ceteth-20 itaconate copolymer, 30% strength in water) from National Starch; Surfactant 193 (Ethoxylated dimethylpolysiloxane) from Dow Corning); Synthalen® W 2000 (acrylates/palmeth-25 acrylate copolymer, 31% in water); Tego Betain L 5045 (cocamidopropyl betaine).

Further compositions disclosed in the European patent application 08151246.9 filed on 11 Feb. 2008 referenced as examples 2 to 7, 9 to 17, 19 to 21, 23, 24, 26 to 35, 37, 39 to 45, and 46—which are incorporated herewith by reference—are also suitable for use in the processes according to the present invention.

Appliances suitable for use in the processes according to the present invention Heat generating hair care appliances suitable for use in the present processes are any conventional appliances currently available onto the market.

The dimensions and values disclosed herein are not to be understood as being strictly limited to the exact numerical values recited. Instead, unless otherwise specified, each such dimension is intended to mean both the recited value and a functionally equivalent range surrounding that value. For example, a dimension disclosed as "40 mm" is intended to mean "about 40 mm."

What is claimed is:

1. A process for reducing hair damage upon treatment of hair by heat comprising the steps of:
   (1) providing a leave-in hair care composition comprising a silicone material and a cosmetically acceptable carrier, wherein the silicone material is a polydimethylsiloxane and is stable at a temperature up to 300° C.;
   (2) applying onto hair a sufficient amount of the hair care composition for treating hair;
   (3) providing a heat generating hair care appliance being a hot surface hair care appliance, wherein the hot surface hair care appliance is a hair dryer, a hot air hair styler, or a hair curler;
   (4) treating hair at a temperature ranging from about 90° C. to about 250° C. using the heat generating hair care appliance for from about 1 min to about 20 min for drying and/or styling hair;
   wherein the polydimethylsiloxane (P) has aminoalkyl groups and has an amine number of at least 0.1 meq/g of polydimethylsiloxane (P), and comprises units of formula I

$$R^1_a R^2_b SiO_{(4-a-b)/2} \tag{I}$$

in which $R^1$ is methyl, an —OR radical, or an —OH radical, $R^2$ are aminoalkyl radicals of formula II

$$-R^3-NR^4R^5 \tag{II}$$

$R^3$ is —(CH$_2$)$_3$—
   $R^4$ is H,
   $R^5$ is —(CH$_2$)$_2$—NH$_2$—,
   a is 0, 1, 2 or 3,
   b is 0, 1, 2 or 3, and
   a+b on average is from 1.5 to 2.5, wherein not more than 9 mol % of the radical $R^1$ is OH or OR.

2. The process according to claim 1, wherein the composition further comprises a protonating agent.

3. The process according to claim 1, wherein the composition further comprises at least one cosmetic hair treatment agent selected from the group consisting of hairstyling polymers, hair-conditioning agents, hair-cleaning agents, and mixtures thereof.

4. The process according to claim 1, further comprising the step of wetting hair with an aqueous composition before, during and/or after applying the hair care composition.

* * * * *